United States Patent [19]
Pribat et al.

[11] Patent Number: 5,017,340
[45] Date of Patent: May 21, 1991

[54] TEMPERATURE COMPENSATED RESISTIVE TYPE SENSOR FOR THE MEASUREMENT OF RELATIVE CONCENTRATIONS OF FLUID REACTIVE SPECIES

[75] Inventors: Didier Pribat, Paris; Joel Perret, Plaisir; Jean-Claude Rouffy, Poissy, all of France

[73] Assignee: Thomson-CSF, Puteaux, France

[21] Appl. No.: 406,305

[22] Filed: Sep. 12, 1989

[30] Foreign Application Priority Data

Sep. 16, 1988 [FR] France ............................. 88 12127

[51] Int. Cl.⁵ .......................................... G01N 27/00
[52] U.S. Cl. .................................... 422/98; 422/68.1; 422/78; 422/80; 422/83; 204/406; 204/424; 73/23.2; 73/23.31; 73/23.32
[58] Field of Search ................... 338/34; 422/98, 68.1, 422/78, 80, 83; 204/406, 415, 424, 425; 73/23.2, 23.31, 23.32

[56] References Cited

U.S. PATENT DOCUMENTS

| | | | |
|---|---|---|---|
| 4,007,435 | 2/1977 | Tien | 338/34 |
| 4,453,397 | 6/1984 | Ohta et al. | 73/23.31 |
| 4,469,626 | 9/1984 | Tuohig et al. | 338/34 |
| 4,697,165 | 12/1987 | Ishiguro et al. | 73/23.31 |

FOREIGN PATENT DOCUMENTS 2908916 9/1980 Fed. Rep. of Germany.
2393302 12/1978 France.

Primary Examiner—Robert J. Warden
Assistant Examiner—Laura E. Collins
Attorney, Agent, or Firm—Oblon, Spivak, McClelland, Maier & Neustadt

[57] ABSTRACT

Disclosed is an oxygen sensor of the resistive type for the measurement of relative fluid concentrations of fluid reactive species. The following are disposed on one and the same substrate:

a sensitive element, the resistivity of which is sensitive to an excess of one of the reactive species;

a thermistor mounted as a resistance bridge with the sensitive element;

a heating resistor fixing the minimum temperature threshold of operation.

Application: The disclosed device can be applied notably to oxygen sensors.

20 Claims, 10 Drawing Sheets

FIG_2

FIG_3

FIG_5

FIG_6

FIG_7

FIG_10

FIG_11

FIG_12

FIG_13

TEMPERATURE COMPENSATED RESISTIVE TYPE SENSOR FOR THE MEASUREMENT OF RELATIVE CONCENTRATIONS OF FLUID REACTIVE SPECIES

BACKGROUND OF THE INVENTION

1. Field of the Invention

The invention concerns a temperature compensated oxygen sensor of the resistive type, for the measurement of relative concentrations of fluid reactive species.

It pertains, notably, to a device capable of producing a signal for the control, in closed loop, of an air/fuel mixture such as the mixtures that feed combustion machines of the internal combustion engine type, or boilers, in particular boilers with forced air circulation.

2. Description of the Prior Art

In recent types of internal combustion engines, particularly in automobile engines with automatic ignition, a marked trend can be seen towards the precise control of the carburation, so as to increase efficiency and performance, on the one hand, and reduce the polluting exhaust emissions on the other hand. In many cases, it is desired to feed the motor with a stoichiometric air/fuel mixture and, in practice, there already are regulation systems that keep this mixture in the stoichiometric state by using an oxygen sensor placed in the exhaust muffler. This sensor delivers a signal representing the state of the mixture given to the cylinders, in indicating whether the mixture in question is rich or lean.

Thus, most of the already existing oxygen sensors deliver a signal of about one volt when the mixture is rich, and a signal of about 50–100 mV when the mixture is lean. The electronic carburation-regulating system therefore works by comparing the value of the output signal given by the sensor, with a voltage reference that is generally located around 500 mV. Under these conditions, if the output voltage from the sensor is greater than 500 mV, which corresponds to a situation where a rich mixture feeds the cylinders, the electronic system for the regulation and servo-control of the engine corrects the fuel injection parameters so as to increase the air/gasoline ratio and, when the output voltage from the sensor is smaller than 500 mV, the electronic system reduces the air/gasoline ratio in such a way that, on the whole, the mixture is always exactly stoichiometric.

In practice, for the vehicles fitted out with trifunctional catalytic mufflers, the carburation has to be regulated by means of an oxygen probe. The standard mechanical settings do not allow the mixture to be kept in a composition range that is narrow enough to be compatible with high efficiency of the catalytic muffler in question.

Two distinct types of oxygen sensors are currently being fabricated or designed: galvanic (or voltaic) sensors and resistive sensors.

Galvanic sensors, which are the most widespread ones, work on the principle of the concentration cell. A glove finger made of stabilized zirconia has its external surface in contact with the exhaust gases, while its internal surface is in contact with an oxygenated reference mixture which is generally air. The internal and external surfaces are provided with electrodes, made of platinum for example, which are used, firstly, to measure the electrochemical potential and, secondly, for the external surface, to catalyze the end of the combustion of the gaseous exhaust mixture.

Various descriptions of this type of sensor will be found in the literature on the subject (H. Dueker, K. H. Friese, W. D. Haecker, Society of Automotive Engineers 1975, paper 750223; H. Y. Gruber, H. M. Wiedenmann, *Society of Automotive Engineers*, 1980, paper 800017; E. M. Logothetis in *Advances in Ceramics*, edited by A. M. Heur and L. W. Hobbs, Vol. 3, *Science and Technology of Zirconia* (American Ceramic Society, Columbus Ohio, 1981, p. 388 etc.).

Resistive sensors work according to a different principle, in that they exploit the properties of variation in resistivity, of certain oxides of transition metals, as a function of the ambient partial pressure of oxygen. Certain allotropic varieties of the oxides of transition metals (for example: Ti, Nb, Ce ...) have, in effect, a resistivity of the form:

$$\rho = \rho o P o_2{}^\alpha \exp W/kt, \tag{1}$$

where:

$\rho o$ is a constant $\rho o_2$ is the ambient partial pressure of oxygen, and k is the Boltzmann constant T is the absolute temperature in Kelvin W is an energy related to the creation of a localized flaw in the crystal lattice of the oxide considered (for example, oxygen defect or interstitial cation)

$\alpha$ is a constant ($\frac{1}{4}$ or 1/6 as the case may be) which is also related to the equilibrium of the flaws in the crystal lattice of the oxide considered.

It is thus seen that, if the partial pressure of oxygen in an exhaust mixture is brought to its thermodynamic equilibrium value (see FIG. 1), a resistor made out of the rutile form of titanium oxide, for example, ($\alpha_{TiO_2} = \frac{1}{4}$) will exhibit a variation in the range of practically four magnitudes when the air/fuel mixture feeding the cylinders touches the stoichiometric point.

It is therefore this property that we shall seek to exploit in the use of resistive type oxygen sensors for the purpose of controlling an air/fuel mixture at the stoichiometric point.

The oxygen sensors based on titanium oxide (rutile form) have been known for about the past 12 years (T. Y. Tien, H. L. Standler, E. F. Gibbons, P. J. Zacmandis, Ceramic Bull., 54, 280, 1975; E. M. Logothetis, Ceramic Eng. and Sci. Proc., 8th Automotive Mat. Conf., 1980; M. J. Esper, E. M. Logothetis, J. C. Chu, Society of Automotive Engineers, 1979, paper 790140; K. Saji, H. Takahashi, K. Kondo, T. Takeuchi, I. Igarashi, Proc. of the International Meeting on Chemical Sensors, Edited by T. Seiyama and Coll., Elsevier 1983, p. 171 etc.)

These sensors take the form of $TiO_2$ disks, in which platinum contact wires have been buried, enabling the value of the resistance of the disk in question to be measured as a function of the partial pressure of oxygen. The drawback of these devices comes from the variations in temperature of the exhaust gases between 300° C. and 900° C. depending on the engine speed. In effect, if we refer to the formula (1) giving the resistivity of titanium oxide, for example, we see that a variation in temperature of 300° C. to 900° C. also produces a variation in resistivity equal to about four magnitudes.

A certain form of temperature compensation must therefore be introduced in order to make it possible to establish a clear distinction between the variations in resistivity due to the variation in the partial pressure of oxygen and the variations in resistivity due to the temperature variation.

Recently, sensors of an "advanced type" have appeared. For these sensors, the techniques of microelectronics and, particularly, silk screen process techniques are used to fabricate sensitive elements made of titanium oxide (W. J. Kaiser, E. M. Logothetis, Society of Automotive Engineers 1983, paper 830167; H. Kondo, H. Takakashi, T. Takeuchi, I. Igarashi, Proc. of the 3rd Sensor Symposium 1983, p. 185; D. S. Howart, A. L. Micheli, Society of Automotive Engineers, 1984, p. 840140; J. L. Pfeifer, T. A. Libsch, H. P. Werthermer, Society of Automotive Engineers, 1985, paper 850381; A. Takami, M. Matsuura, T. Sekiya, T. Okawa, Y. Watanabe, Society of Automotive Engineers, 1985, paper 850381).

The sensors thus described are made with inks or pastes having the desired oxide ($TiO_2$, $CeO_2$, $Nb_2O_3$ etc...) in the form of a suspension in an organic medium suited to a silk screen process type of forming operation. This ink is then deposited on a substrate that is a good electrical insulator and is chemically inert, of the alumina type. It is deposited according to a determined geometry and undergoes appropriate heat treatment enabling the deposit to be given the desired characteristics, particularly as regards porosity.

However, the working point, in temperature, is chosen by means of a heating resistor placed on the rear face of the alumina substrate and making it possible to keep the sensitive element in a relatively narrow range of temperature (of the order of 100° C.) irrespectively of the exhaust gases.

The invention pertains to an advanced type of sensor that integrates the following elements on one and the same chemically inert, electrically insulating, ceramic substrate:
(i) an element sensitive to the partial pressure of oxygen;
(ii) a temperature compensation thermistor;
(iii) if necessary, a resistor enabling the value of the thermistor to be adjusted;
(iv) a heating resistor;
(v) connection means.

SUMMARY OF THE INVENTION

The invention therefore concerns a resistive type sensor for the measurement of relative concentrations of fluid reactive species comprising the following elements, made in thin layers or thick layers, on a substrate 1:
at least one sensitive element, the resistivity of which is sensitive to an excess of one of the reactive species with respect to a determined stoichiometry;
at least one thermistor undergoing temperature variations proportionate to the temperature variations undergone by the sensitive element, this thermistor being mounted as a resistance bridge with the sensitive element;
a heating resistor heating the sensitive element and the thermistor and fixing a minimum temperature threshold of operation.

Moreover, the invention has a certain number of particular sensor structures that are advantageous as regards fabrication.

BRIEF DESCRIPTION OF THE DRAWINGS

The different objects and characteristics of the invention will appear in greater detail in the following description made by way of example and with reference to the appended figures, of which.

DETAILED DESCRIPTION OF THE INVENTION

By using an assembly of the divider bridge type, with a thermistor arranged in series with the sensitive element, it is possible to remove the effects of temperature.

Figure 2:
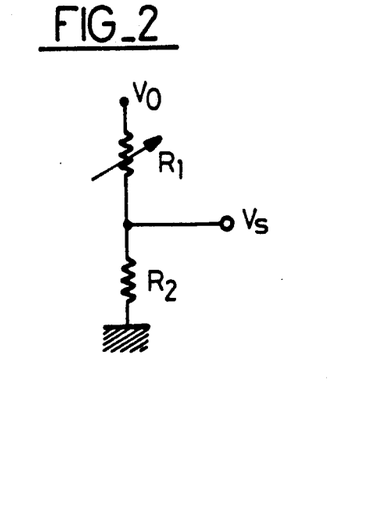
FIG. 2 shows an electrical diagram of a temperature compensation divider bridge.

FIG. 2 shows this type of divider bridge. In this diagram, the resistor $R_1$, made of titanium oxide for example, has a structure that is porous enough to be sensitive to the variations in oxygen pressure, and forms the sensitive element of the device.

The resistor $R_2$, forming the temperature compensation resistor, also prepared with titanium oxide, has a very dense structure. This has the effect of making it practically insensitive to oxygen pressure variations. Its different surfaces can, moreover, be passivated, thus making this compensation resistor wholly independent of variations in oxygen pressure. Under these conditions, the voltage Vs is written: $V_S = V_o R_2/(R_1+R_2)$ where $V_o$ is a fixed voltage chosen by the user. The resistor $R_2$ which, it was stated, had been made insensitive to variations in oxygen pressure, is written in the form:

$$R_2 = K_2 \exp W/kT$$

where: $K_2$ is a constant bringing into play geometrical parameters as well as a fixed oxygen pressure.

Figure 1:
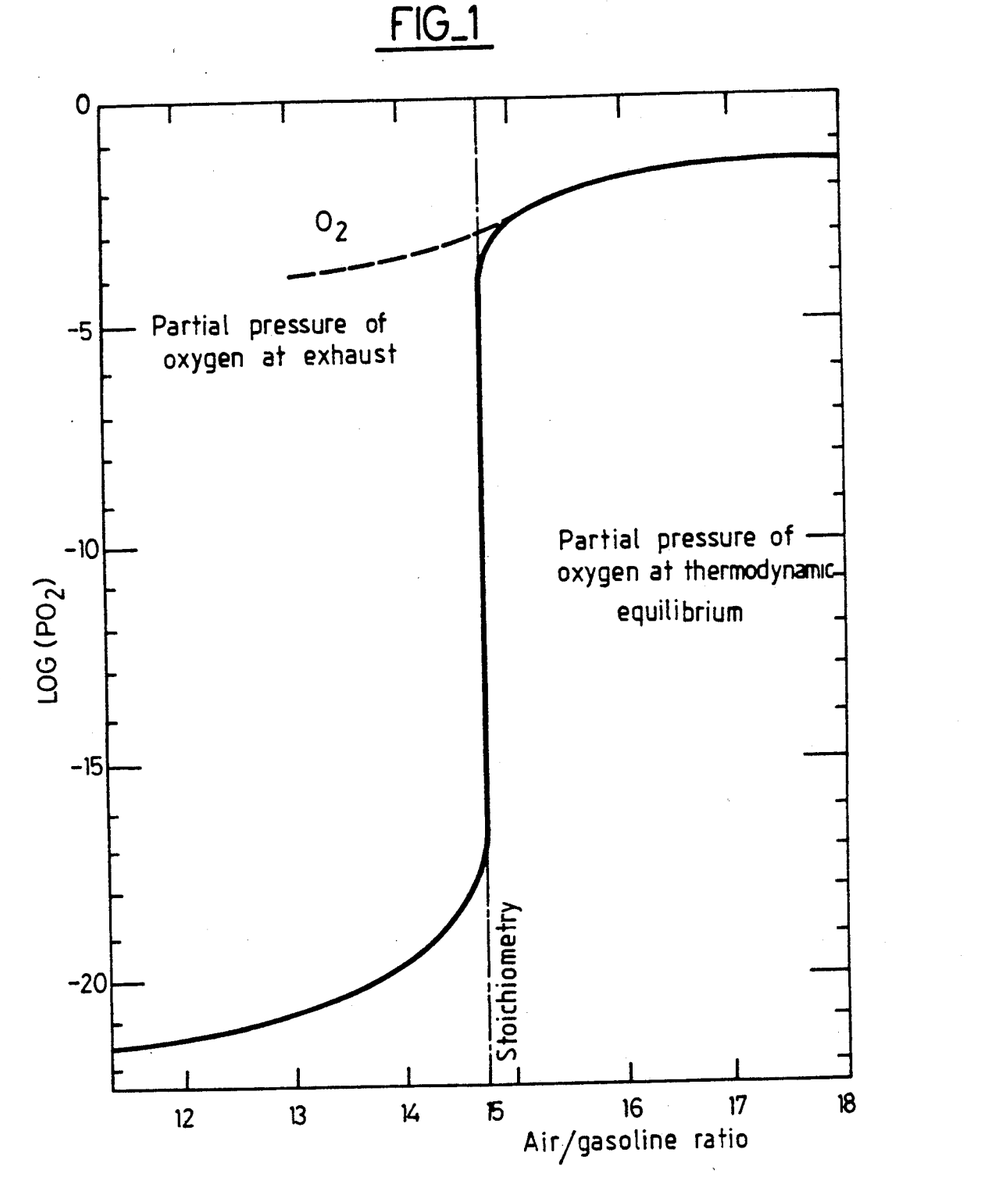
FIG. 1 shows a curve representing the thermodynamic equilibrium of an air/gasoline mixture.
Figure 3:
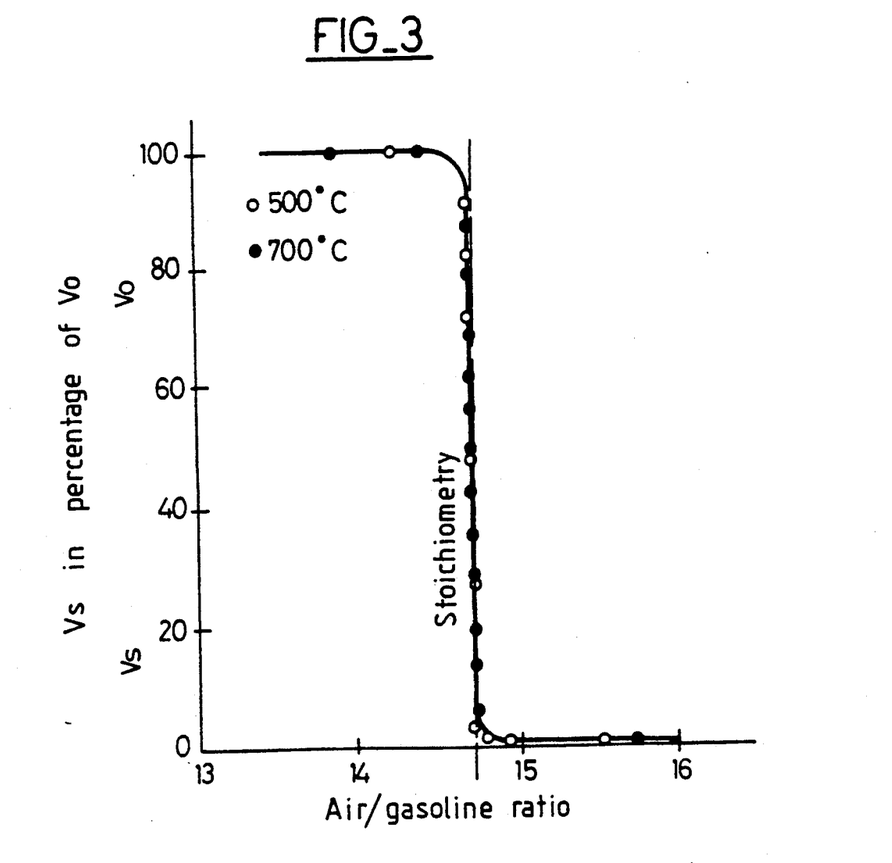
FIG. 3 shows a response curve of a resistive type sensor with temperature compensation according to the invention.

Furthermore, R is written in the form:

$$R_1 = K_1 P_{O_2} \exp W/kT$$

where:
$K_1$ is a geometrical constant
and: $P_{O_2}$ is the ambient pressure of oxygen.
The voltage $V_S$ is then written:

$$V_S = V_o K_2(K_1 P_{O_2} + K_2)$$

and it is seen that it becomes independent of the temperature. If the partial pressure of oxygen at the exhaust is low (less than $10^{-18}$ atmospheres, corresponding to a rich mixture illustrated in FIG. 1), we have $K_1 P_{O_2} < K_2$ and $V_S = V_S = V_o$. If, on the contrary, the mixture is weak, $P_{O_2}$ at the exhaust will be will be of the order of $10^{-2}$ atmospheres, and if $K_1$ and $K_2$ are chosen correctly, $V_S$ may reach a value equivalent to a small fraction of $V_o$. The response of a temperature compensated device such as this is given in FIG. 3. In practical terms, two disks made of $TiO_2$ are placed in series. These disks are fabricated with oxide powders having different grain sizes, and have platinum connections. The structure of the sensitive element is extremely porous while that of the thermistor is very dense. Moreover, to further differentiate the sensitivity to oxygen, the sensitive element may be impregnated with a solution of chloroplatinic acid. After thermal treatment, the platinum remains in an extremely divided form and has the effect of accelerating the placing of this sensitive element in equilibrium (effect of catalysis).

Figure 4:
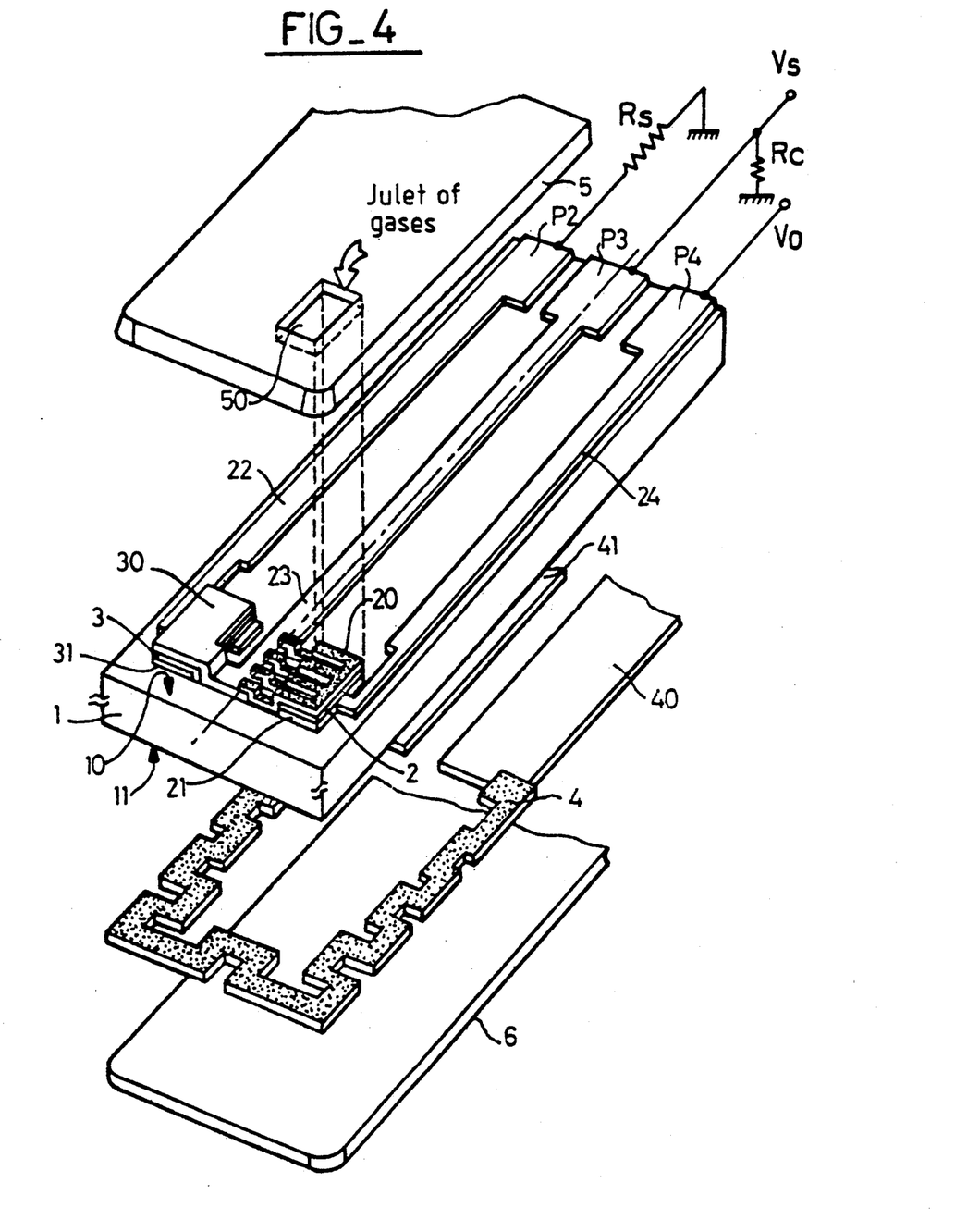
FIG. 4 shows an exemplary embodiment, in a detailed exploded view, of a sensor according to the invention.

FIG. 4 represents a drawing of a sensor according to the invention.

The different materials are deposited in thin layers (by the well known methods of vacuum deposition) or in thick layers (by silk screen process).

The sensor of FIG. 4 has, on the face 10 of a chemically inert substrate, an element 2 that is sensitive to the oxygen content of a gas that it receives. This sensitive element 2 is enclosed by two electrodes 20 and 21. One of them (the electrode 20 in FIG. 4) enables the gases that have to be analyzed to reach the sensitive element 2. These electrodes 20 and 21 are connected by connection tracks 23, 24, one of them being connected to an input potential $V_o$ and the other being connected to a resistor $R_c$ and to a signal output and giving, at this output, a potential signal $V_S$ to user circuits (not shown).

In the vicinity of the sensitive element 2, there is a thermistor 3 that is connected by electrodes 30 and 31, firstly to the connection track 23 and, secondly, to the connection track 22 leading towards a resistor $R_S$ and the ground.

The thermistor 3 is made of a material such that, during a variation in temperature, its variation in resistance is substantially equivalent to that of the sensitive element 2.

Preferably, the thermistor 3 is made of one and the same element as the sensitive element 2.

The set formed by the face 10 of the substrate and the devices that it supports, as has just been described, is covered by an encapsulation layer 5 (made of enamel for example) which is impervious to the gases to be analyzed and thus shelters, notably, the thermistor 3 from the influence of the gases. This encapsulation layer is deposited, for example, by silk screen process. An aperture 50, provided for in the layer 50, enables the access of the gases towards the sensitive element 2.

The face 11 of the substrate 1, opposite the face 10, has a heating resistor 4 that can be connected by connection tracks 40 and 41 to electrical supply circuits (not shown). This resistor 4 enables the sensitive element 2 to be taken to a minimum working temperature. The face 11 and the resistor 4 are covered with an encapsulation layer 6, made of enamel for example.

It is seen, therefore, that the sensitive element 2 (made of the rutile form of titanium oxide for example) is placed in series with the thermistor 3.

This thermistor 3 is fabricated with the same material as the photosensitive element 2. The resistors $R_c$ and $R_S$ make it possible to adjust the range of variation of $V_S$ as a percentage of $V_o$, i.e. to obtain, for example, $V_S = 0.99 V_o$ when the mixture is rich and $V_S = 0.01 V_o$ when the mixture is lean. These resistors, in the form of materials capable of undergoing the silk screen process, can be integrated into the substrate in that part of this substrate supporting the computer connections.

The thermistor 3 is covered with an encapsulation layer which thus isolates it from the external atmosphere.

Thus, its constituent material may have the same grain size at the outset, undergo the same thermal treatment operations and, finally, have the same final microstructure as the sensitive element 2 which, for its part, is in direct contact with the exhaust gases, through the window 3 made for this purpose in the encapsulation enamel 5.

The sensitive element 2 may be made of titanium oxide $TiO_2$ for example. Its structure is porous so as to enable an easy diffusion of the exhaust gases. Its thickness is small for the same reason. This element is between a lower electrode 21, made of a noble metal (platinum for example), and a comb-shaped upper electrode 20 which may be made of either platinum or a platinum-based cermet ($Pt/Al_2O_3$, $Pt/MgAl_2O_4$, $Pt/ZrO_2$). The comb shape of this upper electrode 20 enables direct access by the gases at the surface of the sensitive element 2. Moreover, the fact that it is made of cermet enables it to be made porous, and to be given a porosity that will develop no further during high-temperature use, with the ceramic framework inhibiting the subsequent sintering of the metal. The conductive connecting tracks 22, 23 may be made of a metal of the same type as that of the electrodes (Pt for example) or else of a different metal, connected to said electrodes.

The thermistor 3 is preferably made of one and the same material as the sensitive element 2. According to the preceding example, the thermistor is, therefore, also made of titanium oxide.

The substrate 1 is made of a material which is chemically inert and is a good electrical insulator (such as alumina, beryllium oxide, spinel etc.).

The resistor 4 deposited on the rear face 11 may be either metallic or made of cermet, depending on the resistivity that it is desired to obtain. It is encapsulated by means of an enamel 6 of the same type as that used for the enamel 5 of the upper face 10. For this upper face 10, the enamel is a devitrifying enamel, so that the definition of the gas sampling window 50 is not affected by an exposure to a working temperature of the order of the thermal treatment temperature of this window (about 900° C.).

The connection tracks 22, 23, 24, 40, 41 end in connection areas into which the connector is plugged (front face and rear face), and the passivation enamel of the layers 5 and 6 naturally does not cover this part of the substrate.

According to the exploded view of FIG. 4, the exemplary sensor of the invention has a detection zone in which the sensitive element is to be located, an intermediate zone (or fixing zone) having solely the connection wires (22, 23, 24, 40, 41), and a connection zone having connection areas P2, P3, P4 on the face 10 and P5 and P6 on the face 11.

Figure 5:
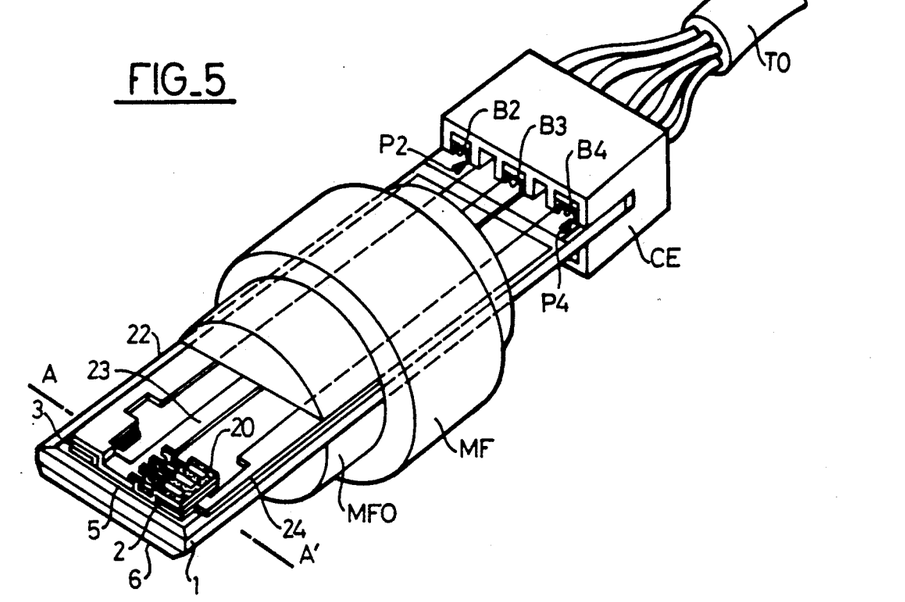
FIG. 5 shows a view in perspective of the sensor of the invention, comprising fixing means and electrical connection means.

Referring to FIG. 5, we shall now describe a more complete exemplary embodiment of the sensor according to the invention. This figure again shows the sensor of FIG. 4.

In the intermediate part, called the fixing zone, located between the detection zone and the connection zone, there is a fixing part MF. This fixing part is fixed rigidly and imperviously to the encapsulation layers 5, 6 of the sensor. The part MF may have a reduced, and possibly threaded, part MFO, enabling the sensor to be assembled in the wall of a casing.

Figure 6:
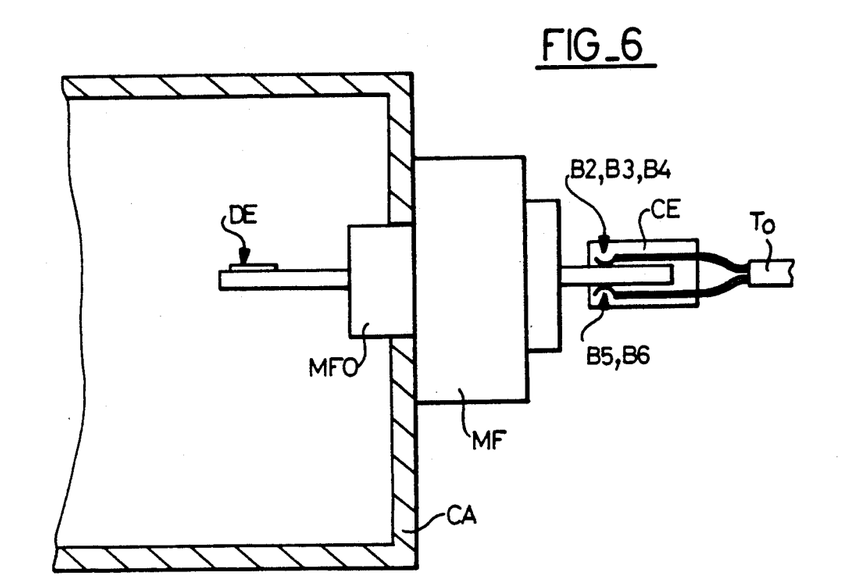
FIG. 6 shows an example of an assembly of the sensor according to the invention.

As shown in FIG. 6, the part MFO of the fixing parts MF is mounted in a casing CA, the cell comprising the sensitive element 2, made at the left-hand end of the sensor, is located inside the casing CA in which the gas mixture to be analyzed and regulated is located. The connector CE is thus isolated from the gas mixture by the fixing part MF and the casing CA.

As shown in FIGS. 5 and 6, a connector CE is plugged into the substrate 1 in the connection zone. Connection elements (B2, B3, B4 for example) are connected to the connection areas (P2, P3, P4) and enable the elements of the sensor to be connected to a cable TO leading towards external circuits that are beyond the scope of the invention.

Figure 7:
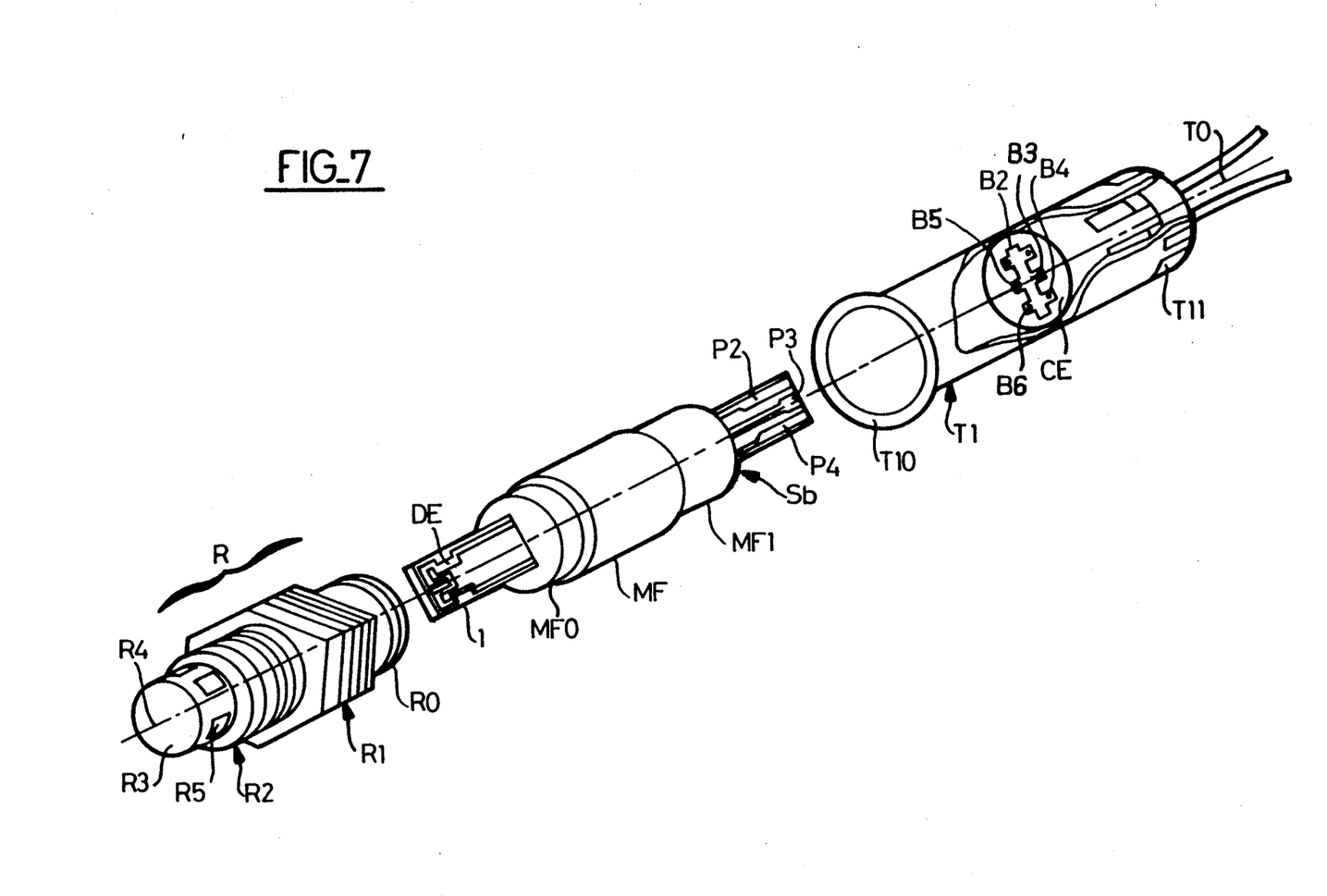
FIG. 7 shows an exploded view of an exemplary embodiment of the sensor according to the invention.
Figure 8:
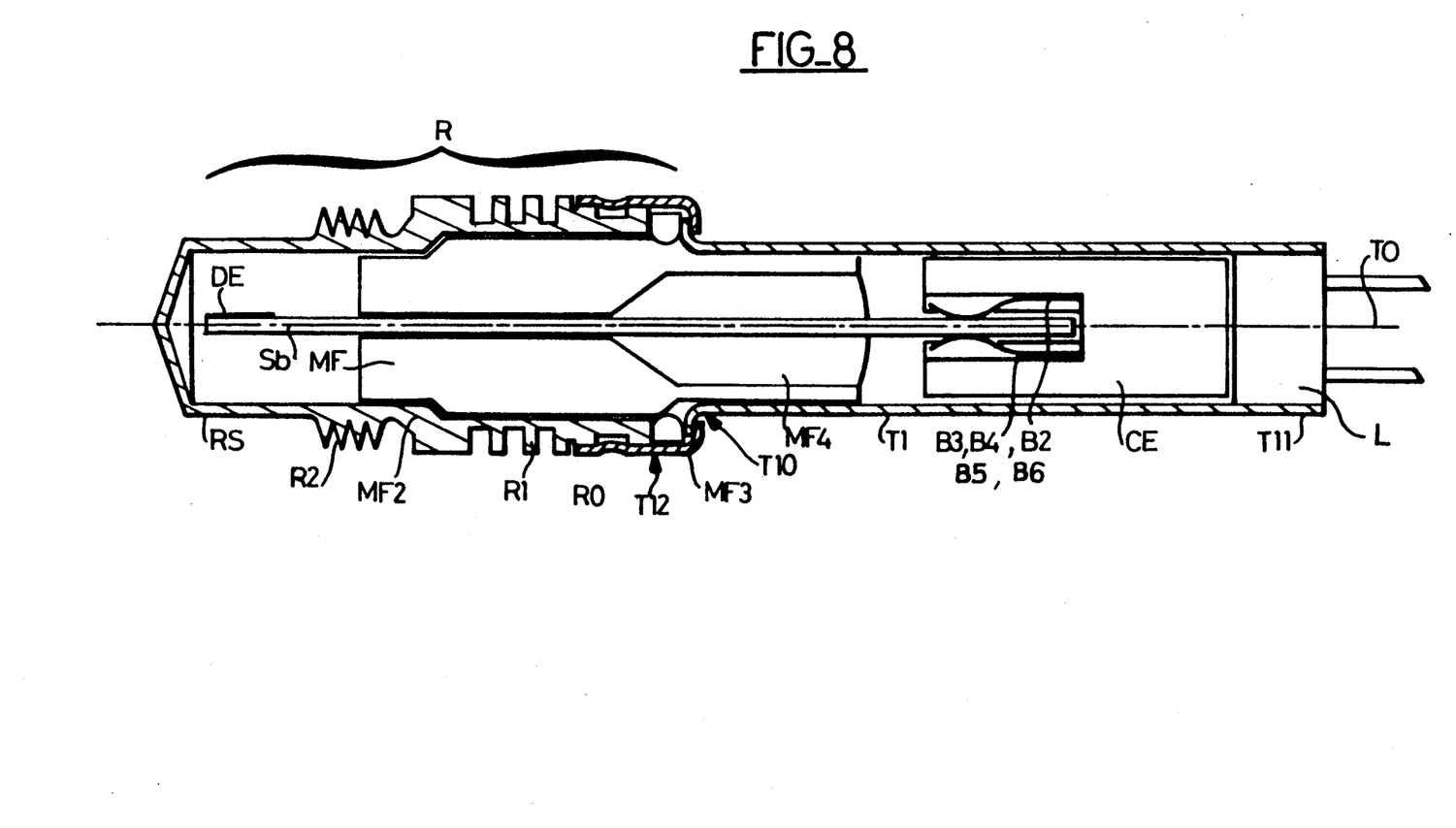
FIG. 8 shows a sectional view of an exemplary embodiment of the sensor according to the invention.

Referring to FIGS. 7 and 8, we shall now make a detailed description of an exemplary embodiment of a sensor according to the invention.

FIG. 7 shows:
- the substrate 1 wafer bearing, notably, the sensitive cell 2, the connection areas P2, P3, P4.
- the fixing part MF comprising fixing parts MF0 and MF1;
- the connector CE, with connection pins B2, B3, B4, B5, B6 and the cable TO The sensor further has a metallic part R to mount the sensor in a casing (not shown). This mounting part enables the mounting of the sensor in a casing instead of the direct mounting of the part MF as shown in FIG. 6.

The mounting part R is hollow so as to receive the wafer 1 and the sensitive element 2 (as well as the thermistor 3). It has:
- a part RO enabling the part MFO to be fitted into the fixing part MF;
- cooling fins R1;
- a threaded part R2 enabling the mounting of the part R in a threaded part of the casing;
- a protective cap R3 protecting the sensitive cell 3 located inside and having apertures R4, R5 for the circulation of the ga to be analyzed.

Besides, a pack T1 is fitted in, by an end T10, to the part MF1 of the fixing part MF. The connector CE is mounted and fixed to the other end T11 and to the interior of the pack T1 in such a way that the pins B2, B3, B4 as well as B5 and B6 are connected to the connection areas such as P2, P3, P4, P5 and P6 of the sensor.

The unit thus described is mounted as shown in a sectional view in FIG. 8. Moreover, the assembly is made impervious in such a way that the exhaust gases do not reach the connection zone of the sensor. To this end, the wafer of the sensor is sealed into the fixing part MF by means of a refractory cement MF4. Seals MF2, MF3 provide for imperviousness between the fixing part MF and the mounting part R, on the one hand, and the assembly part R and the pack T1 on the other hand.

The pack T1 is crimped in its part T10 by a ring T12 and, in its part T11, respectively on the mounting part R and on a plastic ring of the viton type V, providing for the passage of the strands forming the cable To. This latter crimping enables the upper part of the sensor unit to be made impervious.

Figure 9:
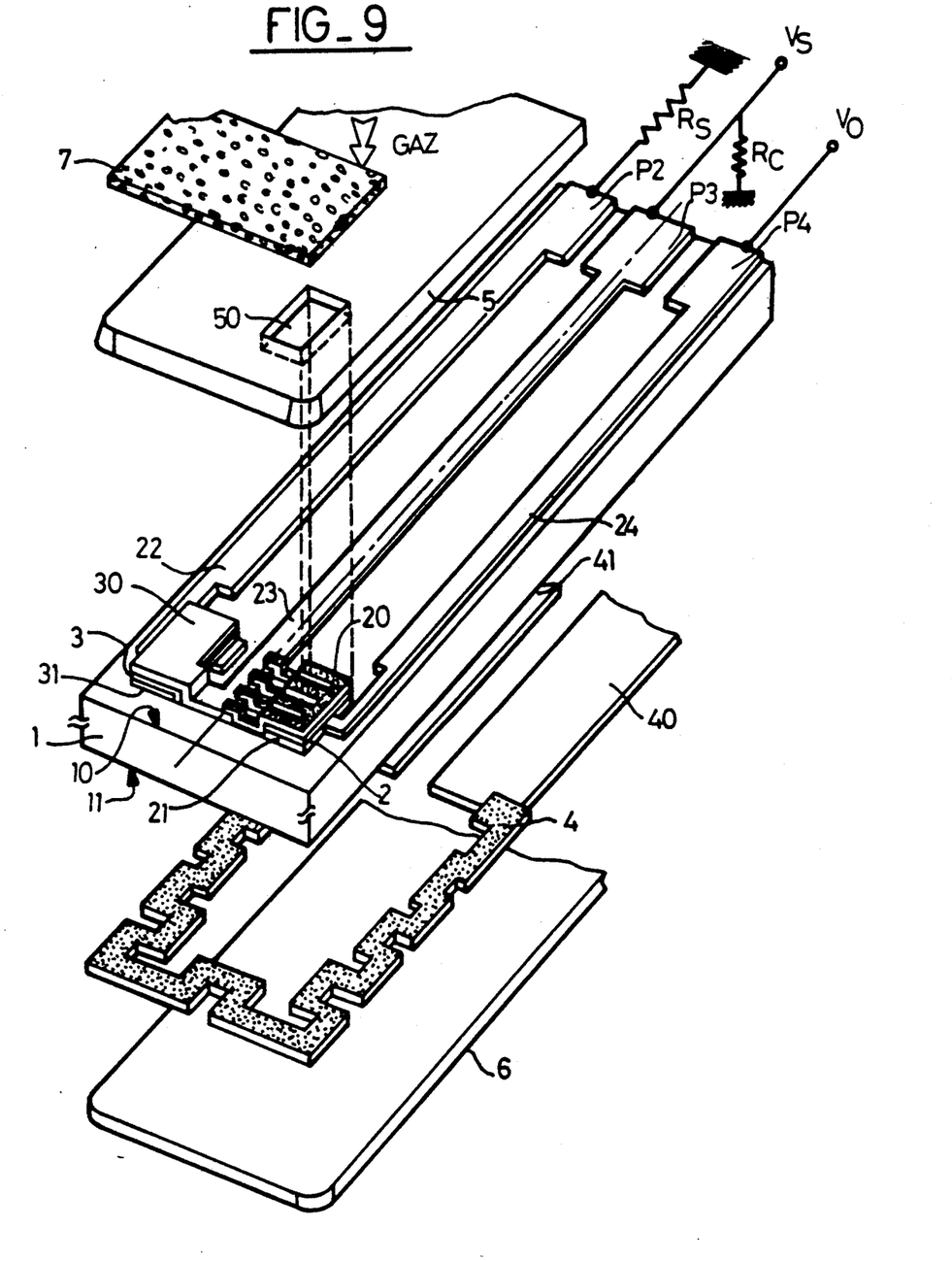
FIG. 9 shows an alternative embodiment of the sensor according to the invention.

In an alternative embodiment of the structure of the invention, shown in FIG. 9, a porous ceramic material 7 ($Al_2O_3$, $Mg\ Al_2O_4$, $ZrO_2$) may be deposited on the upper electrode of the sensitive element. This deposition may be done by silk screen process or by plasma torch, the effect of which will be to limit the flow of gas arriving by the sensitive element 2 and to increase its catalytic activity, hence to reduce the response time for setting up equilibrium.

Furthermore, the sensitive element 2 may also be impregnated by means of a chloroplatinic acid solution, again to increase the catalytic activity and, correlatively, to reduce the response time.

Figure 10:
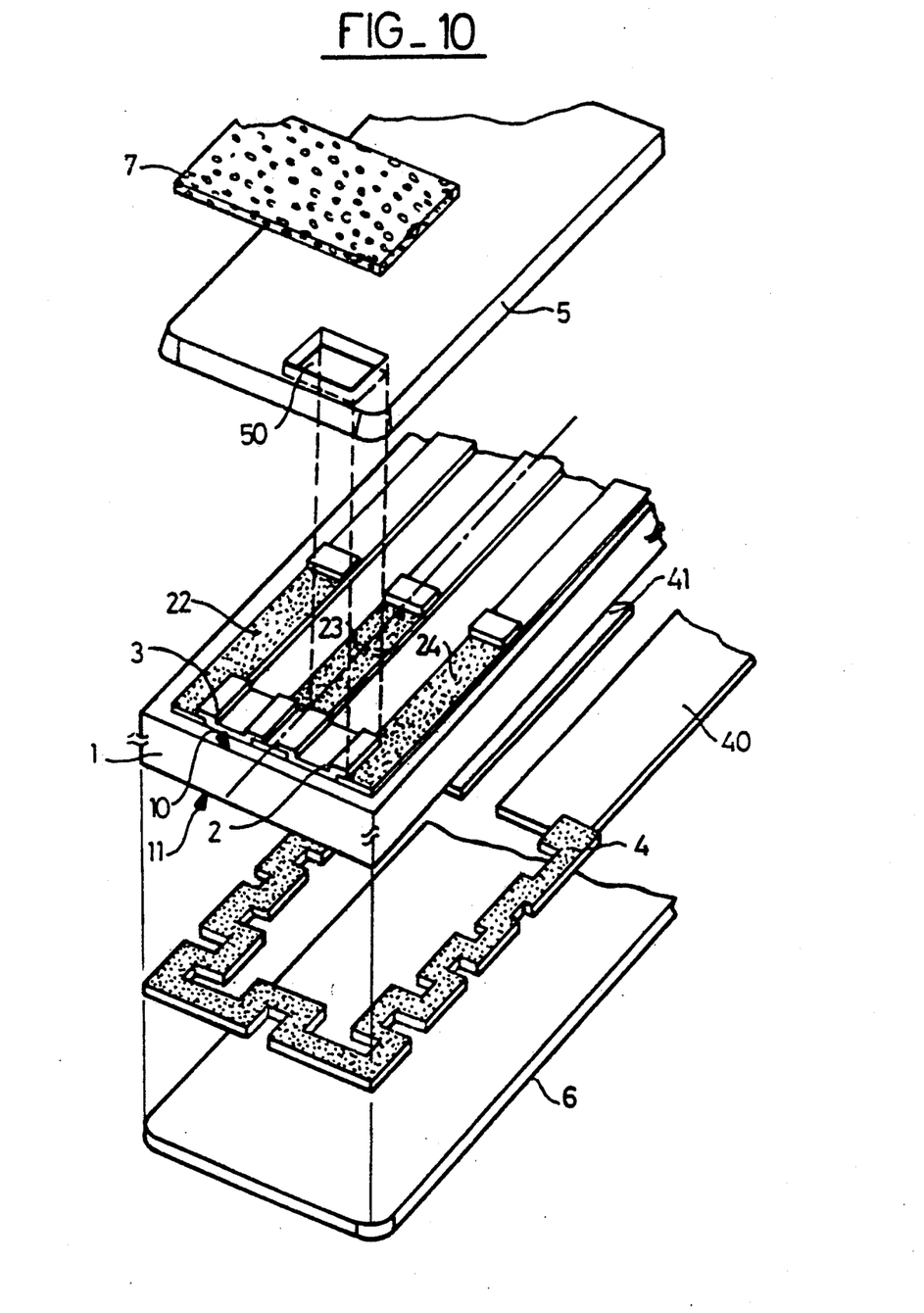
FIGS. 10 and 11 show other alternative embodiments of the sensor according to the invention.

According to another variant, at the structural level, it is possible to use "planar" electrodes as shown in FIG. 10.

The sensitive element 2 and the thermistor 3 are made by planar technique in the same way; the sensitive element 2 overlaps the connection tracks 23-24 and the thermistor 3 overlaps the tracks 22-23.

Figure 11:
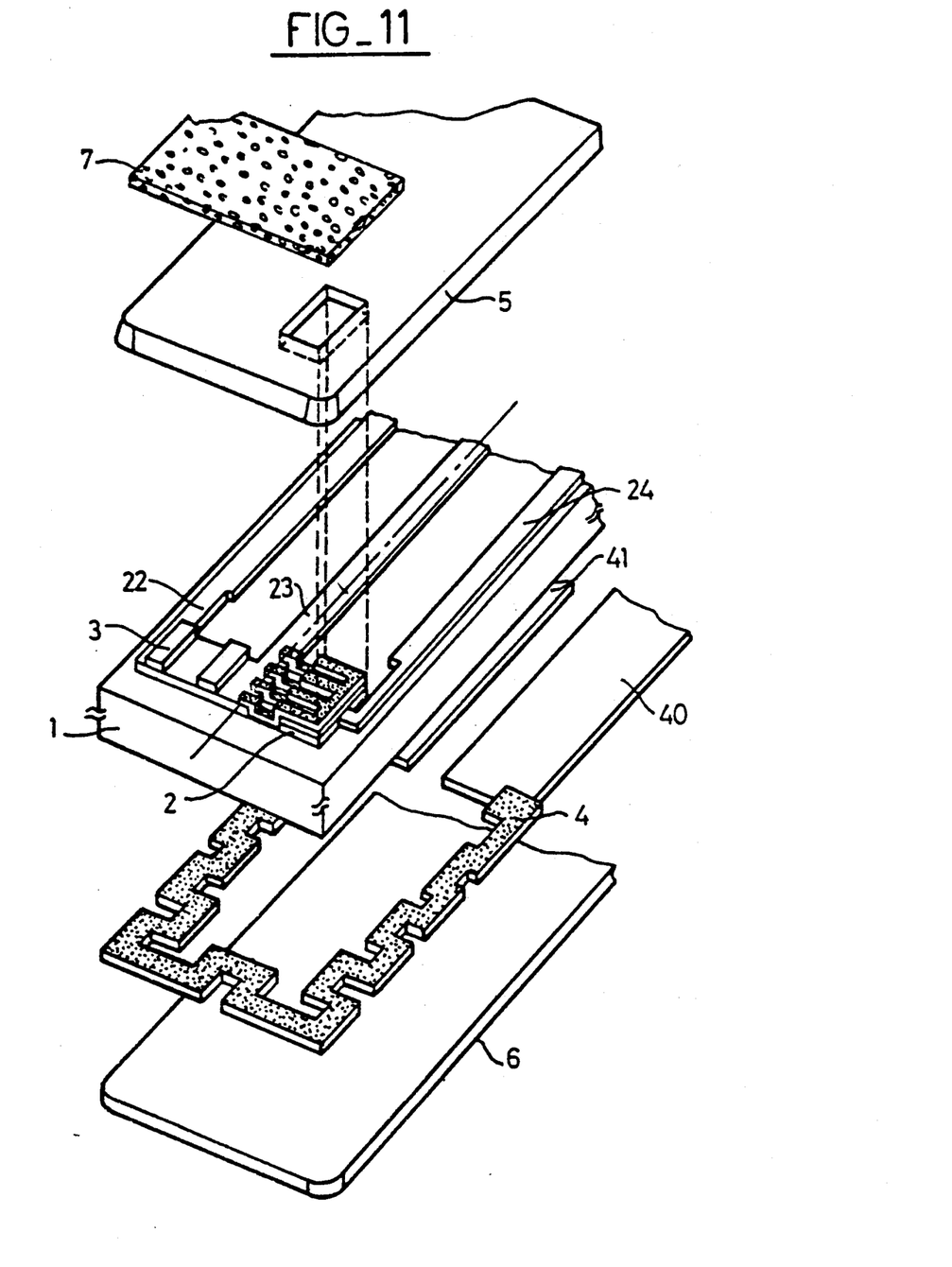

It is also possible, as shown in FIG. 11, to make the sensor according to the invention in the form of a combination of planar electrodes and electrodes superimposed to have a disequilibrium between the values of the resistors of the sensitive element and the value of the thermistor, and to increase the dynamic range of $V_S$ as a function of $V_o$. The sensitive element 2 then has the structure of the sensitive element of FIG. 4, while the thermistor 3 has the structure of the thermistor of FIG. 10. It is also quite clear that the reverse is possible, and that the sensitive element 2 can be given the configuration it has in FIG. 10, and that the thermistor can be given the configuration it has in FIG. 4. Thus, in choosing the geometries in such a way that $R_2$ (corresponding to the thermistor 3) on the divider bridge of FIG. 2 is of the order of 10 K$\Omega$ at 600° C. for example, and $R_1$ (corresponding to the value of the sensitive element 2) is of the order of 100 $\Omega$ when the mixture tilts over to the rich side, and the order of 1 M $\Omega$ when the mixture tilts over to the weak side (always at 600° C.), a variation is obtained, for $V_S$, of between 0.99 $V_o$ and $10^{-2}$ $V_o$ when passing by the stoichiometric point.

A sensor, such as this, according to the invention has advantages, as regards fabrication, because of its integrated structure under impervious encapsulation layers. It is easier to mount and to use this structure.

It has both a compensation thermistor and a heating resistor. The fact of having a heating resistor 4 makes it possible to maintain the sensitive element at a temperature that is always greater than or equal to 500° C. and, therefore, the reactions for putting the gases into equilibrium are faster and there is, therefore, a shorter response time.

The encapsulation of the series thermistor represents an original feature in the sense that it enables the same grain size of material to be used and the same thermal treatment operations to be performed on the sensitive element and on the thermistor without taking special precautions to make the thermistor more dense.

Figure 12:
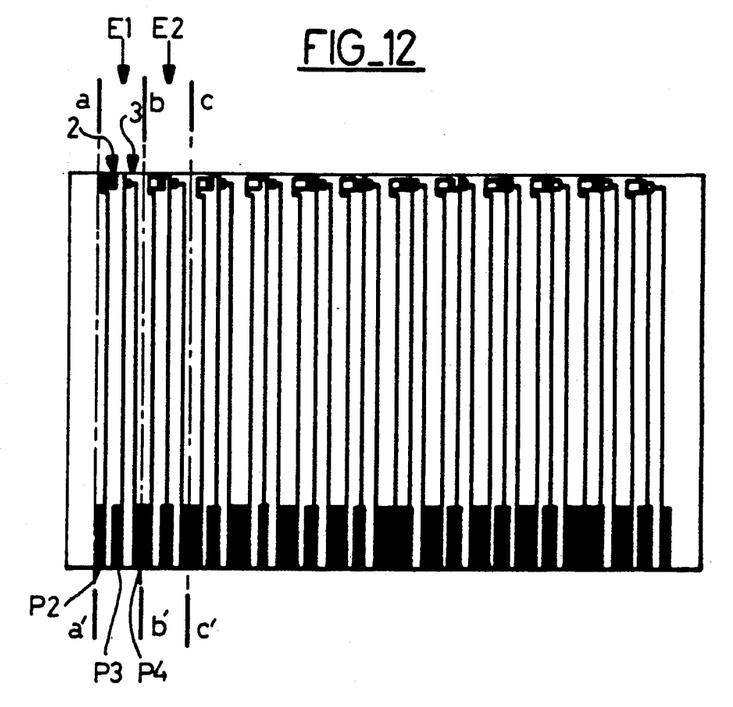
FIGS. 12 and 13 shows a exemplary embodiment of the grouping, on one and the same wafer, of several cells according to the invention.
Figure 13:
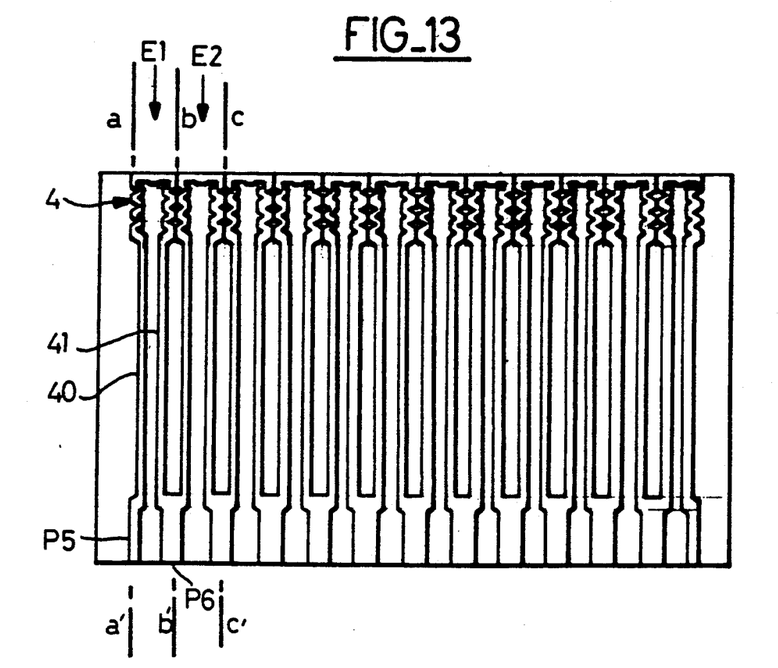

FIGS. 12 and 13 represent an embodiment with a grouping of strips bearing the sensitive elements.

Several cells, E1, E2, are made, side by side on one and the same substrate wafer. As shown in FIG. 12, several evenly spaced out cells, such as E1, are obtained in this way. Each of these cells has, on one face, its sensitive element 2, its thermistor 3, its connection tracks 22, 23, 24 and its connection areas P2, P3, P4.

FIG. 13 shows the opposite face of the wafer, bearing the sensitive elements and the thermistors. On this face, there are resistors, such as those located in zones each corresponding to a cell such as E1, as well as the conductors of 40, 41 and connection zones P5, P6.

The wafer is cut out along lines represented by dots and dashes aa', bb', cc' so as to obtain a sensor bearing, on one face, a cell and the corresponding connections and, on the other face, a resistor 4 and the corresponding connections.

All the sensors obtained are identical.

By way of example, the materials used for the making of sensor such as this could be:
- for the sensitive element: a titanium oxide based material;
- for the electrodes: a cermet material (ceramic/metal alloy);
- for the connection elements and conductors: metallic layers;
- for the encapsulation layers and the material providing for imperviousness between the fixing part MF and the wafer of the sensor: a refractory sealing enamel;
- for the substrate: a material such as alumina with a percentage of it between 80% and 99%.

In the case of an embodiment with a grouping of several sensors on one and the same wafer, the method of the invention provides, after the heat treatment of the enamel, for the cutting out of the wafer to obtain the different individual sensors in the form of strips.

The fixing and supporting part MF should be made of a material with an expansion coefficient matching that of the substrate 1. For example, if the substrate is made of alumina, the part MF will preferably be made of alumina too. Similarly, the sealing cement MF4 will be made of material with an expansion factor matching that of the materials of the part MF and of the substrate 1.

It is quite clear that the above description has been made purely as a non-restrictive example and that other variants may be considered without going beyond the scope of the invention.

Notably, the substrate 1 bearing the sensitive element 2 and the thermistor 3 can be made in the form of a wafer, but it could have any other form.

What is important is that the thermistor should undergo the same variations in temperature as the sensitive element 2 and that it should, if necessary, be thermally coupled to the sensitive element 2.

The numerical examples and the choices of materials, in particular, have been given only to illustrate the description.

WHAT IS CLAIMED IS:

1. A resistive sensor for the measurement of relative concentrations of fluid reactive species comprising the following elements, made in layers, on a substrate:
   - at least one sensitive element, the resistivity of which is sensitive to an excess of one of the reactive species with respect to a determined stoichiometry;
   - at least one thermistor undergoing temperature variations proportionate to the temperature variations undergone by the sensitive element, this thermistor being mounted as a resistance bridge with the sensitive element;
   - a heating resistor for heating the sensitive element and the thermistor and fixing a minimum temperature threshold of operation.

2. A sensor according to claim 1, wherein each thermistor is placed in the vicinity of a corresponding sensitive element.

3. A sensor according to claim 1, wherein each thermistor is made of one and the same material as each sensitive element and is isolated from the fluid reactive species to be analyzed.

4. A sensor according to claim 1, wherein each sensitive element is made in the form of a layer included between two electrodes, with the electrode located on the incoming side of the fluid reactive species to be analyzed having apertures.

5. A sensor according to claim 1, wherein each thermistor is made in the form of a layer located between two connection electrodes.

6. A sensor according to claim 1, wherein each thermistor and each sensitive element comprise planar layers.

7. A sensor according to claim 1, comprising:
   - the substrate having an elongated shape and comprising, placed lengthwise, a first detection zone, a second zone for supporting and fixing the sensor, and a third electrical connection zone;
   - the at least one sensitive element, at least one of which is sensitive to an excess of one of the reactive species with respect to a determined stoichiometry, being disposed directly in the first zone of the substrate;
   - electrical connection areas located in the third electrical connection zone;
   - conductive tracks of electrical connections deposited on the substrate and connecting the at least one sensitive element, the at least one thermistor and the heating resistor to the electrical connection areas located in the third electrical connection zone;
   - an encapsulation layer, made of a material that is impervious to said gas mixture, covering at least the first and second zones, encapsulating notably the at least one sensitive element and the conductive tracks and having at least one aperture providing access for the gases to the first zone;
   - a fixing part located in the second fixing zone and preventing the passage of the fluid from the first zone to the third zone.

8. A sensor according to claim 7, wherein the fixing part is imperviously fixed to the sensor.

9. A sensor according to claim 7, wherein the fixing part has mounting means, enabling the sensor to be fixed to a wall of a casing in such a way that each sensitive element is located inside a casing containing the gas mixture to be analyzed and that the wall of the casing associated with the fixing part prevents the gas mixture from passing into the connection zone.

10. A sensor according to claim 7, comprising a female connector mounted on the third electrical connection zone and having connection pins put into contact with said connection areas.

11. A sensor according to claim 1, wherein the substrate and the fixing part are made of material with matching expansion coefficients.

12. A sensor according to claim 7, wherein the substrate and the fixing part are made of alumina.

13. A sensor according to claim 7, wherein the substrate bearing the sensitive element is sealed into the fixing part by means of a cement, the material of which has an expansion coefficient matching that of the material of the substrate and that of the material of the fixing part.

14. A sensor according to claim 7, comprising a mounting part in which there is mounted the fixing part, with each sensitive element housed in the mounting part, said mounting part further having a threaded element, that enables a fixing in a casing, and cooling fins to cool the mounting part.

15. A sensor according to claim 8, wherein several sensors are made together on one and the same wafer substrate, and then cut out to obtain separate individual functioning sensors.

16. A sensor according to claim 7, wherein each element sensitive to an excess of one of the reactive species as well as each thermistor are implanted on one face of the substrate, and wherein, on the opposite face of the substrate, there is implanted a heating resistor facing a zone of access for the gases.

17. A sensor according to claim 1, wherein said at least one sensitive element and said at least one thermistor have mutually proportionate variations of resistivity with temperature.

18. A sensor according to claim 17, comprising said at least one thermistor having a passivated surface thereby making said at least one thermistor insensitive to variations in oxygen pressure.

19. A sensor according to claim 17, wherein said at least one sensitive element and said at least one thermistor both are comprised of titanium oxide and both have a variation of resistivity R with temperature of the form:

$$R = KP_o \exp W/kT,$$

wherein K is a geometric constant, $P_o$ is the ambient pressure of oxygen, W is an energy related to the creation of a localized flaw in the crystal lattice of an oxide, k is the Boltzmann constant, and T is absolute temperature in Kelvin.

20. A sensor according to claim 17, comprising said at least one sensitive element being made of porous titanium oxide and said at least one thermistor being made of dense titanium oxide.

* * * * *